United States Patent
Rebro

(10) Patent No.: US 12,183,178 B2
(45) Date of Patent: *Dec. 31, 2024

(54) VITALS MONITORING HANDCUFF APPARATUS

(71) Applicant: Zachary Owen Rebro, Lynden, WA (US)

(72) Inventor: Zachary Owen Rebro, Lynden, WA (US)

( * ) Notice: Subject to any disclaimer, the term of this patent is extended or adjusted under 35 U.S.C. 154(b) by 304 days.

This patent is subject to a terminal disclaimer.

(21) Appl. No.: 17/378,657

(22) Filed: Jul. 17, 2021

(65) Prior Publication Data

US 2023/0013865 A1    Jan. 19, 2023

(51) Int. Cl.
  *G08B 21/04*    (2006.01)
  *A61B 5/00*    (2006.01)
  (Continued)

(52) U.S. Cl.
  CPC ........ *G08B 21/0453* (2013.01); *A61B 5/0022* (2013.01); *A61B 5/02055* (2013.01);
  (Continued)

(58) Field of Classification Search
  CPC .............. G08B 21/0453; A61B 5/0022; A61B 5/02055; A61B 5/14552; A61B 5/681; A61B 5/02427; A61B 5/0816; E05B 75/00

See application file for complete search history.

(56) References Cited

U.S. PATENT DOCUMENTS 8,839,796 B2 * 9/2014 Reese ............... H05C 1/00
  128/875
10,458,154 B2 * 10/2019 Caprino ............ E05B 75/00
(Continued)

FOREIGN PATENT DOCUMENTS

CN   206309163 U * 7/2017
CN   107411727 A * 12/2017
(Continued)

*Primary Examiner* — Yingchuan Zhang
*Assistant Examiner* — Laura Hodge
(74) *Attorney, Agent, or Firm* — Nathanial P. Potter

(57) ABSTRACT

A vitals monitoring handcuff apparatus comprising a housing structure that is adapted to be coupled with a set of handcuffs and to contain a plurality of modules and units; a first module that is located within the housing structure and adapted to measure a wearer's heartrate via a sensor; a second module that is located within the housing structure and is adapted to measure the wearer's respiration rate via a sensor; a controller unit that is located within the housing structure, is configured to relay instructional programs to the modules and units which causes the modules and units to operate, and the controller unit receives data from the modules and inputs that data into associated algorithms that produce corresponding output signals; a communication unit that is located within the housing structure and receives the output signals from the controller unit and is adapted to relay the output signals to a user; and a rechargeable power unit located within the housing structure that is accessed by a port on an exterior of the housing structure, provides power to the vitals monitoring handcuff apparatus's other modules and units, and having a receiver which connects with an exterior power source via the port.

22 Claims, 4 Drawing Sheets

(51) Int. Cl.
  *A61B 5/0205* (2006.01)
  *A61B 5/024* (2006.01)
  *A61B 5/08* (2006.01)
  *A61B 5/1455* (2006.01)
  *E05B 75/00* (2006.01)

(52) U.S. Cl.
  CPC .......... *A61B 5/14552* (2013.01); *A61B 5/681* (2013.01); *A61B 5/7405* (2013.01); *E05B 75/00* (2013.01); *A61B 5/02427* (2013.01); *A61B 5/0816* (2013.01); *A61B 2560/0214* (2013.01); *A61B 2560/0252* (2013.01)

(56) References Cited

U.S. PATENT DOCUMENTS

| | | | |
|---|---|---|---|
| 10,480,909 B1 | 11/2019 | Brown | |
| 11,286,693 B2 * | 3/2022 | Heiney | E05B 75/00 |
| 11,406,330 B1 * | 8/2022 | Baldwin | G06V 40/15 |
| 2013/0012795 A1 | 1/2013 | Moenning | |
| 2014/0355167 A1 | 12/2014 | Reese et al. | |
| 2017/0196469 A1 * | 7/2017 | Han | A61B 5/7257 |
| 2019/0033043 A1 * | 1/2019 | Piccioni | A41D 1/005 |

FOREIGN PATENT DOCUMENTS

| | | | | |
|---|---|---|---|---|
| KR | 101938989 B1 | 4/2019 | | |
| WO | WO-2017114471 A1 * | 7/2017 | ............ | A61B 5/053 |
| WO | WO-2018233315 A1 * | 12/2018 | ............... | A61B 5/01 |

* cited by examiner

VITALS MONITORING HANDCUFF APPARATUS

FIELD OF THE INVENTION

The present invention relates to an improved set of handcuff devices having a number of features which facilitate the collection and presentation of biometric data of a wearer. These features may include, for example, measuring the heartrate of the wearer, measuring the surface temperature of the wearer's skin, measuring the blood pressure of the wearer, measuring the respiration rate of the wearer, providing the location data of the wearer, those features being controlled and analyzed by a controller unit, and the handcuff device having a communication unit that displays or alerts a law enforcement official to a possible medical situation of the wearer.

BACKGROUND OF THE INVENTION

Physical restraints, such as handcuffs or other bindings, are often used by law enforcement officials to restrain a detained individual. Often, these devices cover areas on an individual's body that are suited to measuring vitals readings, such as handcuffs covering a wearer's wrists. Currently, prior to transporting a restrained individual, law enforcement officials are trained to manually take vital readings and/or wait for emergency medical service providers to arrive for assessment when a restrained individual shows signs of a medical issue. Additionally, even with proper training, it may be difficult for a law enforcement official to assess and constantly monitor the physical condition of a restrained individual. This is especially true when the law enforcement official is transporting a restrained individual who did not present signs of a medical issue prior to the law enforcement official placing the restrained individual in the vehicle. Thus, there is a long-felt need for a device which can simultaneously restrain an individual, monitor that individual's vital signs, and provide data and/or alerts to the law enforcement official for emerging or present medical issues.

SUMMARY OF THE INVENTION

The following presents a simplified summary of the present invention to provide a basic understanding of the invention's concepts. This summary is not an extensive overview, and it is not intended to identify critical elements or to limit the scope of this discloser. The sole purpose of this summary is to present some general concepts in a simplified form as a prelude to the detailed description of the invention.

The subject matter disclosed and claimed herein, in one embodiment of the present invention, comprises a vitals monitoring handcuff apparatus that monitors a wearer's vital signs and displays data and/or alerts law enforcement officials of emerging or present medical issues. For example, the vitals monitoring handcuff may comprise one or more of the following modules in addition to the three units: a respiration rate (breaths-per-minute) sensor module; a heartrate sensor module; a temperature sensor module; an activity level module; a blood pressure module; a global position system ("GPS") module; a controller unit that controls and collects data from the aforementioned modules and then analyzes the data collected and sends an output; a communication unit which may display information, produce an alarm, and/or transmit an alert to a corresponding receiver or program (such as an app on a computer or smart phone); and a power unit which powers the other modules and units.

In a further embodiment of the present invention, an optical heartrate sensor or plurality of sensors, one that uses photoplethysmography ("PPG"), is disclosed. The PPG sensor or sensors receive instructions from the controller unit and measures the wearer's heartrate by measuring artery volume using a light emitter and detector system. A plurality of light signals is sent by an emitter and the light reflected by the wearer's artery is captured by a detector. The system measures a change in the amount of light reflected based on the volume of the wearer's artery prior to, during, and after the wearer's pulse wave. The data measured by the PPG is sent to the controller unit which uses that data to calculate the wearer's heartrate.

In a further embodiment of the present invention, an optical respiration sensor, one that uses photoplethysmography ("PPG"), is disclosed. The PPG sensor receives instructions from the controller unit and measures the wearer's respiration rate by measuring artery volume using a light emitter and detector system. A plurality of light signals is sent by the emitter and the light reflected by the wearer's artery is captured by the detector. The system captures a change in the amount of light reflected based on the volume of the wearer's artery prior to, during, and after the wearer's pulse wave. The data measured by the PPG is sent to the controller unit which uses that data to calculate the wearer's respiration rate.

Alternatively, in some embodiments of the present invention, a bioimpedance sensor is disclosed. The bioimpedance sensor receives instructions from the controller unit and measures the wearer's respiration rate by measuring the resistance of the wearer's skin to an exposure of electrical current. The data measured by the bioimpedance sensor is sent to the controller unit which uses that data to calculate the wearer's respiration rate.

In a further embodiment of the present invention, a dermal temperature sensor is disclosed. The dermal temperature sensor measures the temperature of the wearer's skin at one or more points and sends that data to the controller unit. The controller unit uses that data to calculate the wearer's temperature based on the data from the dermal temperature sensor. In further embodiments of the present invention, the vitals monitoring handcuff device includes an ambient temperature sensor that does not make contact with the wearer. This ambient temperature sensor measures and sends the ambient temperature to the controller unit which may use the ambient temperature data in an algorithm with the data from the dermal temperature sensor to more accurately determine the wearer's body temperature.

In a further embodiment of the present invention, an activity level module which detects multiple states of the wearer such as a stationary or inactive state and a movement or active state. The activity level module sends corresponding signals to the controller unit which processes the data into a digestible form so that the wearer's activity level is determinable during a period of time. The activity level module may include one or more of the following: an accelerometer, a gyroscope, a rotary encoder, a calorie measurement sensor, a heat sensor, a moisture measurement sensor, a displacement sensor, a pedometer, an altimeter, and combination of the foregoing, or any similar device which measures displacement, rotation, or a change on the wearer's skin.

In a further embodiment of the present invention, the vitals monitoring handcuff device includes a GPS module. This system is useful for locating the wearer of the vitals monitoring handcuff apparatus. Law enforcement officials will appreciate the novelty and usefulness of having a set of physical restraints with a GPS module in the event that the law enforcement officials need to locate the wearer. Also, it will be appreciated by those skilled in the art that the present invention may be built with tamper and damage resistant materials and structures. Additionally, the GPS module may be useful for the controller unit's calculations.

In a further embodiment of the present invention, the vitals monitoring handcuff device includes a controller unit. The controller unit comprising at least a processor, a computer memory storage unit, a volatile memory unit, and circuitry to interconnect the components of the controller unit. The processor executes the instructions to the modules to collect data, receives the data from those modules, inputs that data into corresponding algorithms to determine the wearer's vitals measurements, and then sends corresponding signals to the communication unit.

In a further embodiment of the present invention, the vitals monitoring handcuff device includes a communication unit. The communication unit comprises at least one of a display screen, a speaker, a Wi-Fi™ communicator, a mobile network communicator, and a Bluetooth™ communicator. The display screen may be comprised of commonly used mobile technology screens such as LED screens or LCD screens. Additionally, the display screen may have a hardened, protective layer or mesh over the screen to reduce potential damage. The communication unit displays or sends a status, signal, or alert regarding the wearer's condition via one of the aforementioned communication apparatuses or methods.

In a further embodiment of the present invention, the vitals monitoring handcuff device includes a rechargeable power unit. The power unit is encased within the housing structure of the present invention; however, the housing structure provides access to the power unit via a port designed to receive power via an external power source. One example of the external power source is a cable which is adapted to couple with the power unit on one end and a wall socket outlet on the other end.

To the accomplishment of the foregoing and related ends, certain illustrative aspects of the disclosed innovation are described herein in connection with the following description and the annexed drawings. These aspects are indicative of only a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The embodiments of the present invention disclosed herein are illustrated by way of example, and not by way of limitation, in the figures of the accompanying drawings, in which like reference numerals may refer to similar elements.

DETAILED DESCRIPTION OF THE PRESENT INVENTION

Figure 1:
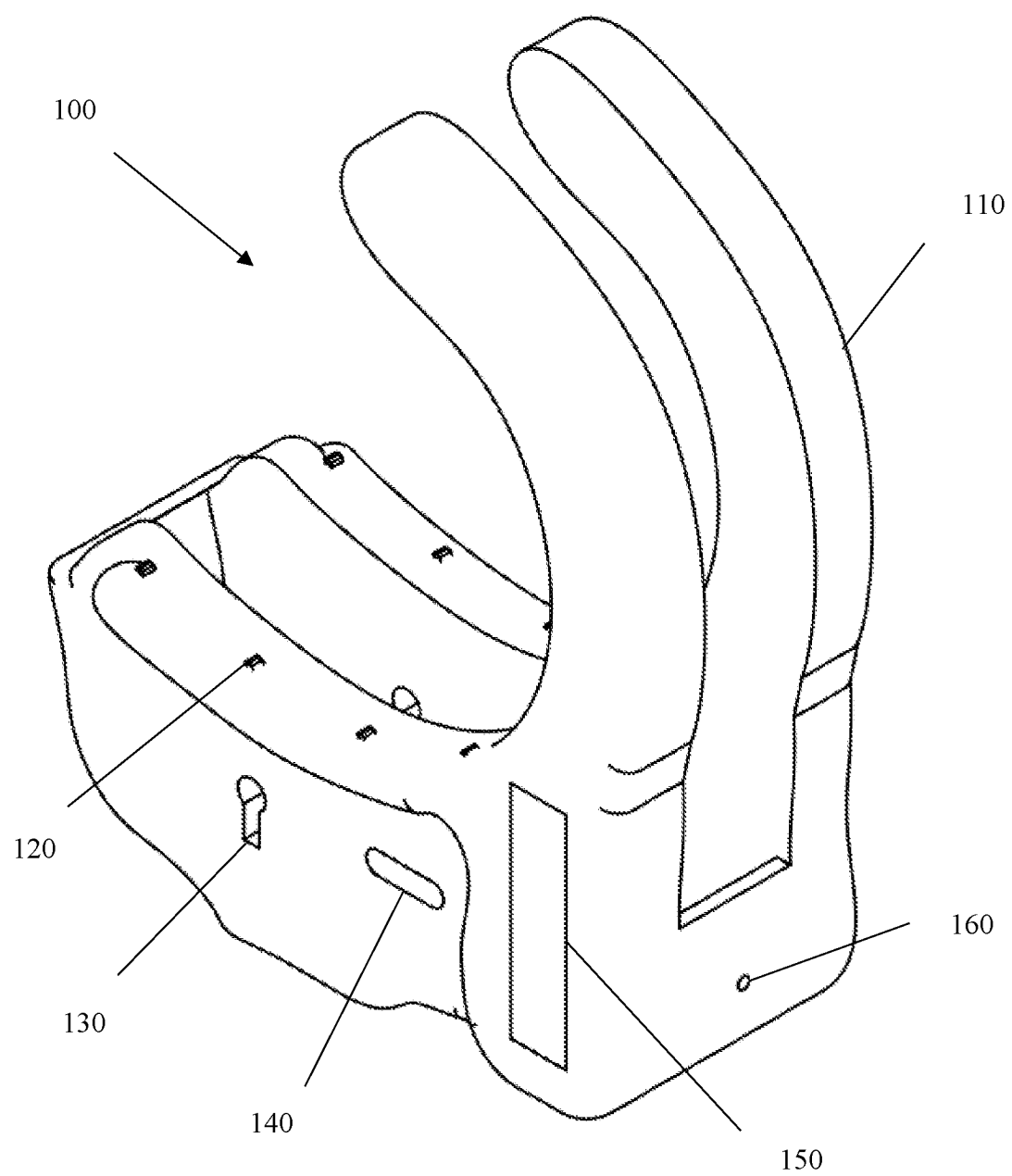
FIG. 1 illustrates the vitals monitoring handcuff apparatus of the present invention in accordance with the disclosed architecture.

The innovation is now described with reference to the drawings, wherein reference numerals are used to refer to elements throughout. In the following description, for purposes of explanation, numerous specific details are set forth to provide a thorough understanding of the present invention. It may be evident that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

As noted above, there exists a long-felt need in the art for a restraining apparatus that can monitor the vitals of a wearer. Moreover, there is a long-felt need for a restraining device that monitors the wearer's vital signs and alerts law enforcement officials (or other users of the present invention) of emerging or present medical issues. Similar vitals monitoring technologies are used in the medical devices and consumer products fields; however, these devices do not offer physical restraint nor are they adapted to alert law enforcement officials of medical issues.

Referring to FIG. 1. In some embodiments, the present invention is a novel vitals monitoring handcuff apparatus 100 that comprises a housing structure 110 that partially encompasses and is coupled to a suitable set of handcuffs. The coupling of the housing structure 110 and the set of handcuffs is configured in a way to allow the set of handcuffs' normal open and close motions. For example, the housing structure 110 will couple with a standard set of handcuffs (such as Armament Systems & Procedures ("ASP") handcuffs). That standard set of handcuffs retains the ability to rotate its rachet system while coupled with the vitals monitoring handcuff apparatus 100. The housing structure 110 is configured in a way that allows it to make contact with the wearer's wrist while the set of handcuffs is in a locked position. The housing structure 110 is a shell that has an exterior and an interior. The interior of the housing structure 110 may be accessed by disassembling the housing structure 110, through access panels, or via the other various holes and ports in the housing structure 110.

The housing structure 110 is adapted to have a keyhole access point 130 and/or secondary access point 140 to a locking mechanism in the set of handcuffs. Additionally, the housing structure 110 is adapted to allow a connection portion of the set of handcuffs to connect, through a gap in the housing structure 110, from one cuff portion to another cuff portion of the set of handcuffs. The connection portion can be a linked metal chain, a cable, a cord, or other suitable connector. The housing structure 110 is made of metal, hard plastic, or other suitable materials which are durable enough to be abused by the wearer without damaging the housing structure 110. Additionally, the housing structure 110 contains more than one sensor module 120, a controller unit, a communication unit, and a power unit. In some embodiments, uncoupling the housing structure 110 from the set of handcuffs may provide access to the interior components comprised of the modules and units of the vitals monitoring handcuff apparatus 100. In further embodiments, the portion of the housing structure 110 that is obscured by the set of handcuffs may further comprise an access panel which shields the internal modules and units from the set of handcuffs. In even further embodiments, the access panel may comprise a plate portion and a locking mechanism that must be disengaged in order for law enforcement officials to access the internal modules and units for maintenance, updates, or repairs between detainments.

In some embodiments, the present invention includes the plurality of sensor modules 120 protruding through to the exterior of the housing structure 110. The sensor modules 120 have an interior portion that is within the interior of the housing structure 110 and an exterior portion that protrudes through the housing structure's 110 exterior so that the sensor module 120 makes contact with the wearer's wrist during detainment. These sensor modules 120 may be one or more of the following: a PPG sensor having one or more emitters and detectors; a bioimpedance sensor; a dermal temperature sensor; a blood pressure measuring system having a plurality of nodes; an serum pressure oxygen (commonly called a "$SpO_2$") sensor; an electrocardiogram ("ECG") sensor; an electrodermal activity ("EDA") sensor; and an array of activity level modules comprised of one or more of an accelerometer, a gyroscope, a rotary encoder, a calorie measurement sensor, a temperature sensor, a dermal moisture measurement sensor, a displacement sensor, a pedometer, and an altimeter. The individual types of sensor modules 120 may be configured as a single sensor or as an array of sensors.

In some embodiments, the sensor modules 120 of the vitals monitoring handcuff apparatus 100 are spaced throughout the portion of the housing structure 110 which makes contact with the wearer's wrist while the vitals monitoring handcuff apparatus 100 is in the locked position during detainment. Those skilled in the art will appreciate that a plurality of sensor modules 120 in such an arrangement as depicted in FIG. 1 will allow the various types of sensors to contact the wearer's wrist while the vitals monitoring handcuff apparatus 100 is not tightened to an undesirable and/or uncomfortable position on the wearer. In further embodiments, the sensor modules 120 are spaced out and configured around the portion of the housing structure 110 contacting the wearer's wrist when in the locked position in such a way that at least one sensor is always touching the wearer. In some embodiments, the controller unit contains a sensor module monitoring program which discerns whether a particular sensor module is touching the wearer due to the received data from the sensor module. For example, if the light emitted and detected by a PPG sensor system sends measurement data to the controller unit showing that the light reflected had too high or low a value, the sensor module monitoring program will instruct the controller unit to disregard the measurement data because it is outside an anticipated range that indicates that the measurement data was not collected while the PPG was making contact with the wearer's wrist. In some embodiments, the sensor modules may be configured to extend beyond the contact point on the housing structure where the sensor modules are affixed to the exterior of the housing structure. This extendable sensor module would allow the sensors to remain in contact with the wearer's skin without the need for the vitals monitoring handcuff apparatus to be too tightly ratchetted on the wearer. In this embodiment, the extendable sensor modules may be configured to extend or retract based on the wearer's wrist movements while the vitals monitoring handcuff apparatus is in the locked position. In further embodiments, the extendable sensor modules further comprise spring mechanisms which control the extension and retraction of the extendable sensor modules.

In some embodiments, the sensor modules 120 are controlled by the controller unit which has a processor, a computer memory storage unit, a volatile memory unit, and circuitry connecting the controller unit to the modules and units within the housing structure 110. The controller unit may be programmed with an operating system and individual programs which control the operation of the modules and units, and calculates the wearer's vital signs by inputting the data from the sensor modules 120 into corresponding algorithms. The controller unit may send an output from the algorithms to a communication unit that will display the wearer's vitals measurements and/or alert the law enforcement official of an emerging or active medical condition of the wearer. Vitals measurements are a form of biometric data. The communication unit can do one or more of the following: display vitals measurements (for example, using a LCD or LED screen 150), play an alert signal through a speaker in the housing structure 110, and send a wireless signal (for example: Wi-Fi™, wireless mobile network, or Bluetooth™) to a program or device that is configured to display data to or alert law enforcement officials of a medical issue of the wearer. One embodiment of the communication unit includes a cellular chip that sends a wireless signal to a receiver or network such as a mobile telephone carrier network or a satellite network. This wireless signal can then be relayed to law enforcement officials on-site or at a designated location. Another embodiment of the communication unit includes a Bluetooth™ chip that sends the wireless signal to a Bluetooth™ receiving device belonging to the law enforcement official, whether on his or her person or to a unit in his or her vehicle.

A PPG sensor operates by at least one emitter emitting an amount of light. The light is reflected by a vein in the wearer's wrist. The reflected light is measured by at least one detector. The emitter is controlled by the controller unit and the detector sends a measurement of the amount of light reflected by the vein to the controller unit. The controller unit inputs the measurement of emitted light and measurement of detected light into an algorithm which calculates the heartrate of the wearer to some degree of accuracy. Additionally, current technology and algorithms are able to estimate the wearer's respiration rate based on the emitted and detector-measured light.

A bioimpedance sensor operates by sending an electrical current through at least one electrode to at least one other electrode. The amount of electrical current sent through the first electrode is instructed by the controller unit. And the data for the amount of current received by the second electrode is sent to the controller unit. In some embodiments, the controller unit then processes the two measurements into an algorithm to calculate the wearer's respiration rate. Bioimpedance sensors have other potential uses for the vitals monitoring handcuff apparatus 100 that those skilled in the art may appreciate such as calculating skin-water content. An array of bioimpedance sensors on the housing structure 110 provides an appreciable benefit to the vitals monitoring handcuff apparatus 100 because individual wearers will have different wrist sizes, bony anatomy, skin-water content, vascular branch size and locations, and ratios of adipose, skin, bone, and muscle content within the array of sensor modules 120. This array of bioimpedance sensors will help ensure the collection and accuracy of data collected and provided to the controller unit.

A dermal temperature sensor measures and sends the measurement of a wearer's skin temperature at a contact point to the controller unit. The controller unit uses this data to calculate the wearer's body temperature. Additionally, an ambient temperature sensor may send a measurement of the ambient temperature to the controller unit so that the controller unit may use these those measurements in an algorithm to more accurately calculate the wearer's body temperature. Alternatively, the controller unit may connect to the internet via a wireless connection and retrieve the reported ambient temperature. The controller unit engages a GPS module to determine the location of the wearer. This engagement and use of the GPS module can serve many purposes. Particularly, a GPS module within the vitals monitoring handcuff apparatus 100 allows law enforcement officials to locate the wearer. This is appreciably useful in the event that the wearer is lost or has fled detainment. Additionally, the controller unit may retrieve the wearer's location using the GPS module in order to determine the ambient temperature at the wearer's location via the internet. The controller unit may use this GPS-located and retrieved ambient temperature measurement in an algorithm with the dermal temperature sensor to more accurately calculate the wearer's body temperature.

A blood pressure measurement system having a plurality of nodes and an inflation system may be used to measure a wearer's blood pressure. The blood pressure measurement system operates by receiving a signal from the controller unit to inflate the inflation system until blood flow through the veins in the wearer's wrist stops. Then, the nodes detect once the blood in the veins in the wearer's wrist begins to flow again at both a systolic pressure and normal blood flow pressure. These measurements are sent to the controller unit which calculates the wearer's blood pressure.

A $SpO_2$ sensor having a plurality of nodes with at least one emitter and at least one detector may be used to measure the amount of oxygen in the wearer's blood. The controller unit causes at least one emitter of the $SpO_2$ sensor to emit an amount of light. The light is reflected by the blood in the wearer's veins. The light is measured in both the red and infrared spectrums. At least one detector measures the reflected red and infrared light and sends this data to the controller unit which inputs the data for the amount of emitted light and the amount of measured reflected light into an algorithm which calculates a measurement of the wearer's blood-oxygen levels.

An ECG sensor measures the small amount of electrical current produced by the action of the wearer's heart pumping blood through the wearer's veins. The ECG sensor sends this data to the controller unit which uses the measurement with an algorithm to calculate the wearer's heart's rhythm and electrical activity.

An EDA sensor measures the changes in electrical activity resulting from changes in the wearer's sweat glands. Changes in measurements of the electrical activity may indicate changes in the stress level of the wearer. The EDA sensor sends its measurement data to the controller unit which may use that data in corresponding algorithms to calculate a stress level of the wearer.

An array of activity level modules comprised of one or more of an accelerometer, a gyroscope, a rotary encoder, a calorie measurement sensor, a temperature sensor, a dermal moisture measurement sensor, a displacement sensor, a pedometer, and an altimeter may be present in the vitals monitoring handcuff apparatus 100 to measure an activity level of the wearer. In some embodiments, it is beneficial to include multiple of the same activity level module components (such as three gyroscopes with each at different orientations) to more accurately calculate activity levels. Where necessary, the controller unit will send instructions to the appropriate activity level modules in order for the activity level modules to collect a measurement of the wearer's activity level. Whether instructed by the controller unit or passively measured by the activity level modules, the data collected by the activity level modules is relayed to the controller unit which inputs the data into corresponding algorithms to calculate the wearer's activity level.

In some embodiments, an access point 160 to a functionality button is present on the housing structure 110. The functionality button may turn the present invention on or off, and it may allow the present invention to enter a "silenced" mode. The functionality button may be configured where a "long press" (applying pressure to activate the button over several seconds) turns the present invention on or off, and "short presses" turns the "silenced" mode on or off. The access point 160 may be configured so that it is so small that a tool (such as a SIM tray ejector tool for mobile phones) is required to interact with the functionality button.

In some embodiments, the vitals monitoring handcuff apparatus 100 may remain in a dormant state awaiting activation to an activated state by a gesture from the law enforcement official or when the controller unit receives a sufficient amount or type of data from one or more of the sensor modules 120. In further embodiments, while in the dormant state, some processes (such as wireless, Wi-Fi™, and Bluetooth™ connectivity, illuminating the display unit, or the active collection of biometric data) are disabled to reduce the amount of power the device latently drains from the power unit. In further embodiments, the vitals monitoring handcuff apparatus 100 remains in the dormant state so long as the set of handcuffs are not ratchetted in a closed position on the wearer. An example of the closed position is when the set of handcuffs are secured around the wearer's wrists so that the wearer cannot remove the handcuffs. In such an embodiment, the vitals monitoring handcuff apparatus 100 includes a sensor that detects whether the set of handcuffs are ratchetted to the closed position on the wearer.

The aforementioned gesture, for example, may be in the form of briefly shaking the device to cause the activity level modules (such as the accelerometer(s), gyroscope(s), or displacement sensor) to produce data to send to the controller unit. The controller unit, in response to the receipt of data from the activity level modules, then switches the device into the activated state and attempts to collect biometric data from the sensor modules and relay that data by transmitting the data via the communication unit and/or displaying the data via the display unit.

The aforementioned sufficient amount or type of data to switch the device from the dormant state to the activated state may be predetermined (and changeable) by a program contained on the controller unit. The controller unit, in response to the receipt of the sufficient amount or type of data, then switches the device into the activated state and attempts to collect biometric data from the sensor modules and relay that data by transmitting the data via the communication unit and/or displaying the data via the display unit.

Figure 2:
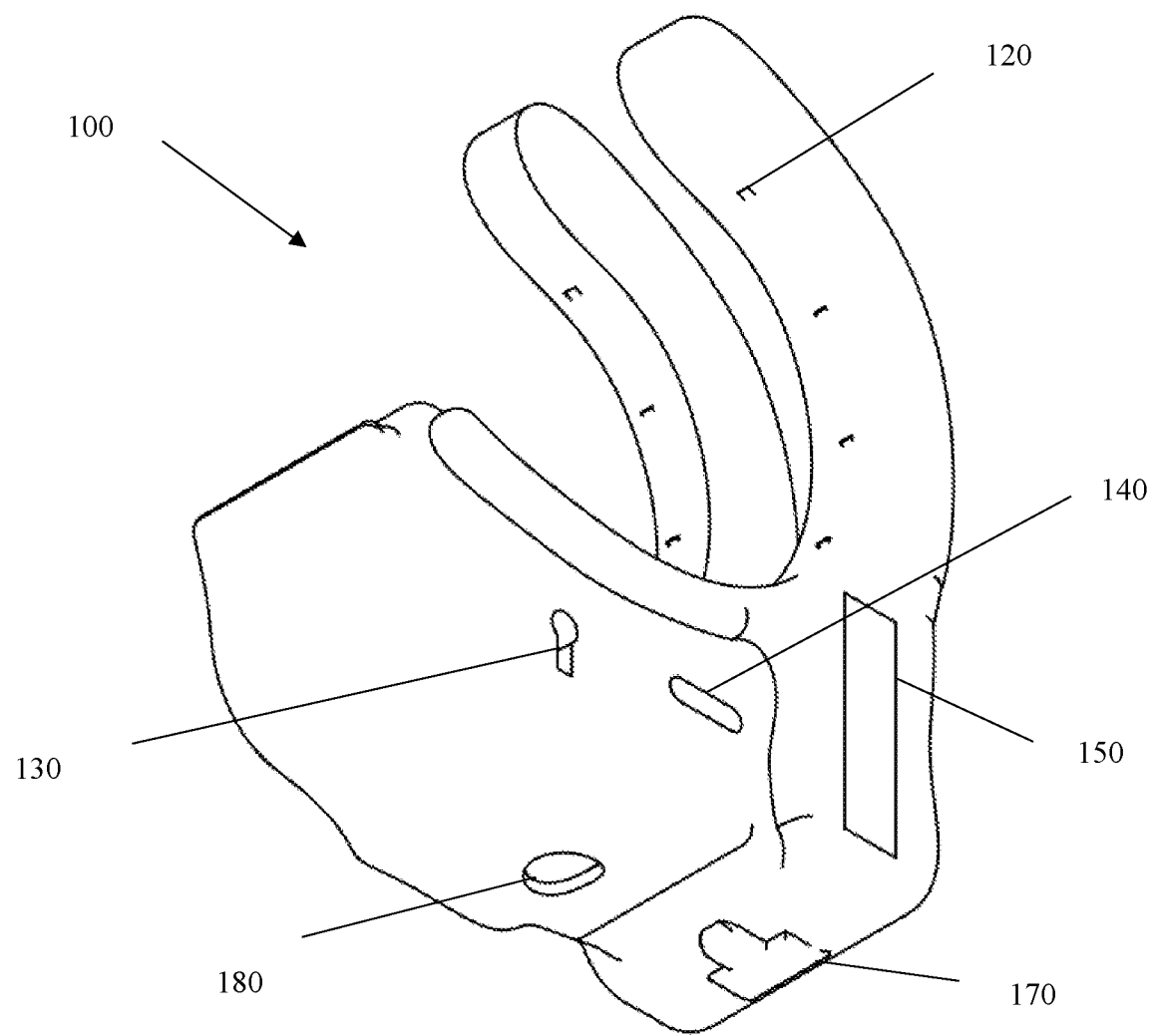
FIG. 2 illustrates another angle of the vitals monitoring handcuff apparatus of FIG. 1.

Referring to FIG. 2. In some embodiments, a power unit is located within the housing structure 110 and provides power to the other units and modules of the vitals monitoring handcuff apparatus 100. In further embodiments, the housing structure 110 is adapted to have a port 170 which couples with a power subsystem to charge the power unit within the housing structure 110. It should be appreciated by those skilled in the art that the port and power sub may be comprised of, in one embodiment, a multipurpose data-transfer and charging connection such as a USB charging connection. The USB charging connection can connect with the power unit to charge the vitals monitoring handcuff apparatus 100 and to the controller unit as an access point which could be used to transfer data to and from the controller unit to an external source such as a computer.

In some embodiments the housing structure's 110 port 170 for the power unit further comprises a cover (such as a rubber-coated panel or gasket between the housing structure 110 and the cover panel) to prevent dust and damage of the power unit's port 170. The cover for the port 170 may also further comprise a locking mechanism such as a magnetic lock, keyhole lock, or electronic lock, for the purpose of preventing tampering with the port 170 on the housing structure 110 of the vitals monitoring handcuff apparatus 100.

In some embodiments a Bluetooth™ pairing button can be included on the housing structure 110. In further embodiments, the Bluetooth™ pairing button is located in an interior wall of the power unit's port 170. The Bluetooth™ pairing button in the interior wall of the power unit's port 170 is located in such a way that it does not conflict with the aforementioned cover of the port 170 nor does it conflict with the charging system within the port 170. Law enforcement officials may access and use the Bluetooth™ pairing button to pair the vitals monitoring handcuff apparatus 100 to a device such as a cell phone or computer.

In some embodiments, a connection hole 180 in the housing structure 110 is present to allow the connection portion of a set of handcuffs to connect one cuff to the other cuff. This connection hole 180 can be narrow enough to only allow the connection portion of the set of handcuffs to fit through the connection hole 180. In such an embodiment, one cuff of the set of handcuffs may need to be disconnected from the connection portion of the set of handcuffs and then reconnected once the cuff is coupled to the housing structure 110. In other embodiments, the housing structure 110 may have a connection hole 180 that is large enough for the cuff of the set of handcuffs to be moved through the connection hole 180 before coupling with the housing structure. In further embodiments, a housing structure 110 with a connection hole 180 that is large enough for a cuff of a set of handcuffs to move through the connection hole 180 may further comprise a locking mechanism that prevents the cuff of the set of handcuffs from being undesirably moved backwards through the connection hole 180.

Figure 3:
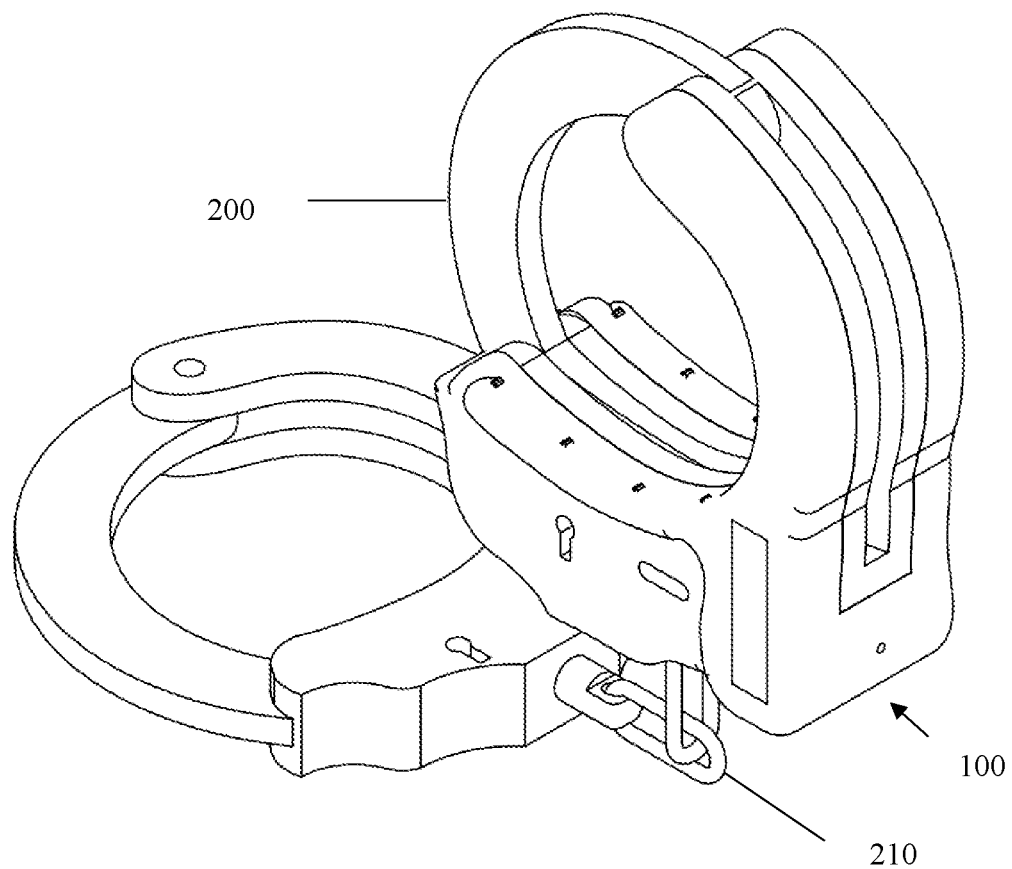
FIG. 3 illustrates the vitals monitoring handcuff apparatus of FIG. 1 coupled with a set of exemplary handcuffs.

FIG. 3. Illustrates an embodiment of the present invention wherein the housing structure 110 is coupled to a standard set of handcuffs 200 (such as ASP handcuffs). One skilled in the art should find it appreciable that the housing structure 110 may be constructed to have a complimentary shape to the set of handcuffs (as depicted in FIG. 3), provides access to the set of handcuffs' 200 keyhole at the keyhole access point 130, and to the set of handcuffs' 200 secondary locking mechanism at the secondary access point 140. As shown in FIG. 3, the complimentary shape of the housing structure 110 should be constructed to resemble at least a portion of the set of handcuffs coupled with the housing structure 110. The embodiment of FIG. 3 also shows a chain link connection 210 between one cuff and the other cuff of the set of handcuffs 200. This chain link connection 210 passes through the connection hole 180 of the housing structure 110. In the illustrated embodiment, the connection hole 180 is not large enough for the cuff of the set of handcuffs to pass through; therefore, this embodiment requires the chain link connection 210 to be attached to the cuff after the cuff has coupled with the housing structure 110.

Figure 4:
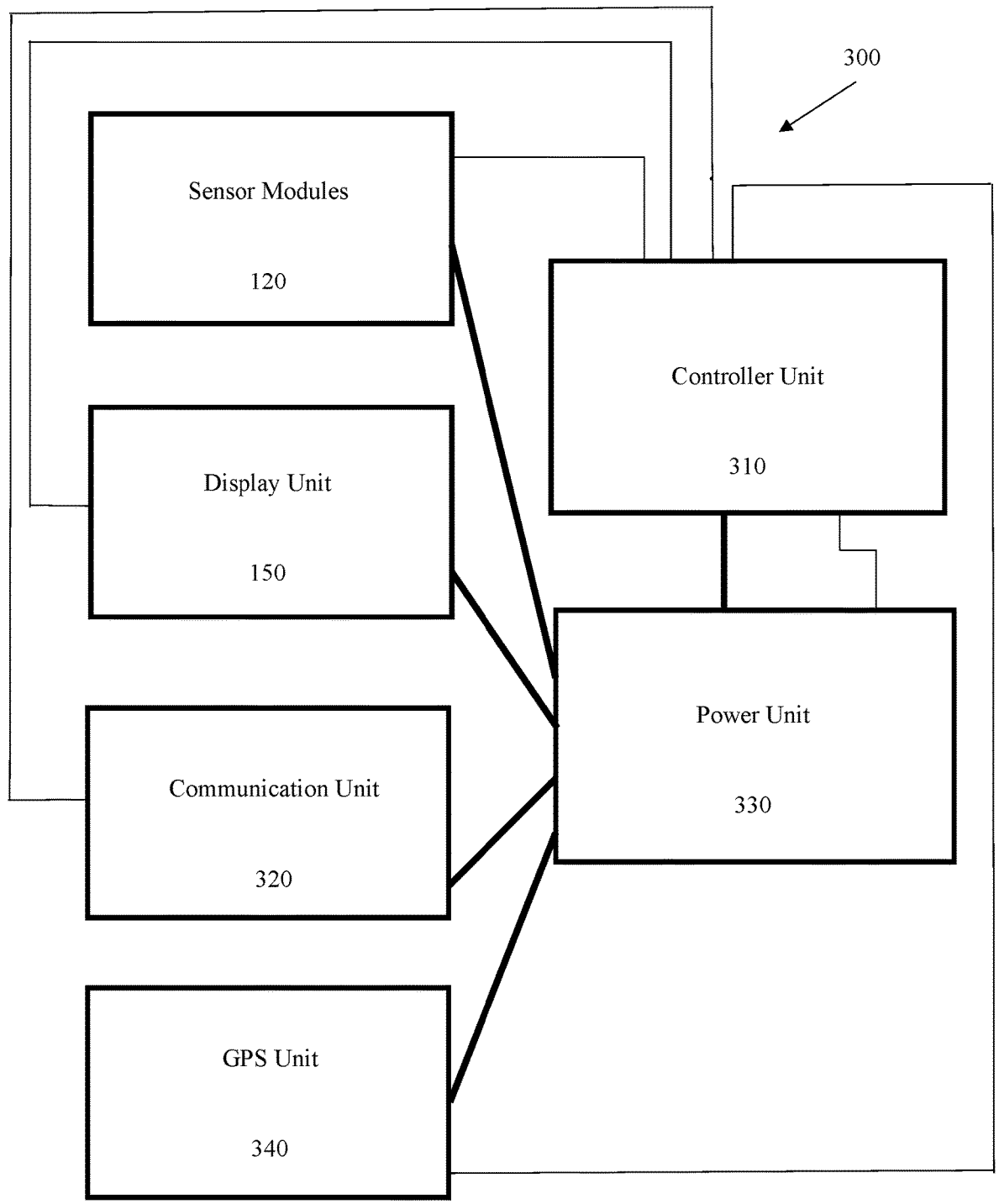
FIG. 4 shows a representational diagram of the circuitry of the vitals monitoring handcuff apparatus depicting the connection of the controller unit to the other modules and units, and the power unit also connected to the other modules and units.

FIG. 4. shows, in some embodiments of the present invention, a configuration of the components within the housing structure 110 of the vitals monitoring handcuff apparatus 100. Sensor modules 120, the display unit 150, the communication unit 320, GPS unit 340, and the controller unit 310 are all connected to and receive electrical power from the power unit 330. The power unit 330 subsequently includes a battery to hold an amount of electrical charge. The battery is charged and recharged by a power subsystem. The power subsystem may comprise known technologies such as a charging port, insertable battery cells, inductive charging (aka wireless or cordless charging), or any other charging system appreciated by those skilled in the art. In some embodiments, the insertable battery cells are also rechargeable by way of an exterior charging station or similarly suited method. In other embodiments, the inductive charging is accomplished by the power unit comprising a battery connected to an inductive charging receiver and that receiver being charged by an inductive charging receptacle that the vitals monitoring handcuff apparatus may be placed on to initiate charging the battery within the power unit. In further embodiments, the inductive charging battery, receiver, and charging receptacle use either tightly-coupled electromagnetic inductive charging (also known as non-radiative charging) or radiative electromagnetic charging. In even further embodiments, the vitals monitoring handcuff apparatus has an inductive charging station designed to hold and charge the vitals monitoring handcuff apparatus. Those skilled in the art will appreciate that, in some embodiments, the vitals monitoring handcuff apparatus 100 will remain usable to restrain the wearer even when the power unit is discharged and cannot power the electrical components of the present invention.

In some embodiments of the present invention, the sensor modules 120, display unit 150, communication unit 320, GPS unit 340, and power unit 330 are controlled by a controller unit 320. The controller unit 320 comprises a processor, a computer memory storage unit, a volatile memory unit, and circuitry. The controller unit 320 may comprise various executable programs used to control the modules and units, additional programs which calculate biometric data based on the data received from the sensor modules, an operating system, and other suitable executables which are necessary for the function of the vitals monitoring handcuff apparatus 100. The controller unit 320 sends instructions to, receives data from, and processes outputs for the other modules and units of the vitals monitoring handcuff apparatus 100.

In other exemplary embodiments of a vitals monitoring handcuff apparatus 100, the housing structure may be constructed onto and permanently affixed to a set of handcuffs. Those skilled in the art will appreciate that the nature of the permanently affixed housing structure is more difficult for a wearer or other individual to tamper with or damage. Additionally, some users may find it appreciable to manufacturing and cost benefits in permanently affixing the housing structure to a set of handcuffs.

In some embodiments of the present invention, a law enforcement official sets the vitals monitoring handcuff apparatus 100 to an "on" mode so that the modules and units are operating and prepared to measure the wearer's vitals measurements and alert the law enforcement official of the wearer's potential medical issues. Next, the law enforcement official takes the vitals monitoring handcuff apparatus 100

(that is coupled to the set of handcuffs) and places the device onto the wearer who is being placed under detainment. The controller unit causes the sensor modules to collect measurements and data, which is relayed back to the controller unit for processing during the detainment. Upon detection of vitals measurements outside of given parameters, the controller unit will cause the communication unit to display the vitals measurements, play an alarm to alert the law enforcement official, and/or transfer the measurements and/or alarm to an external receiver such as an app on a smartphone or computer that may display the vitals measurements or alert the law enforcement official of any. The law enforcement official may place the device into its "silent" mode once the alert has sounded so that the alter does not continue to sound as the law enforcement official determines and executes an appropriate course of action. Finally, after the vitals monitoring handcuff apparatus 100 has been removed from the wearer, the law enforcement official may recharge the device by connecting it, at the port, to a power subsystem.

It should be understood that the term law enforcement official may be referred to in the singular or the plural but will have the same meaning. It should also be understood that law enforcement official or officials are interchangeable with "user" if the device is used by another individual who is not a part of any body of law enforcement.

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one of ordinary skill in the art without departing from the scope of the present invention. Several such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A vitals monitoring apparatus coupled with a set of handcuffs comprising:
   (a) a housing structure having an exterior and interior, adapted to be coupled and uncoupled with the set of handcuffs used by a law enforcement official for detainment of a wearer, the interior of the housing structure containing a plurality of modules and units, the exterior of the housing structure constructed to generally have a complimentary shape to the set of handcuffs, the exterior of the housing structure configured to contact the wearer's wrist while the set of handcuffs is engaged in a locked position on the wearer's wrist during detainment, and the housing structure being constructed to allow access to the set of handcuff's locking mechanism;
   (b) a first sensor module having an interior portion of the first sensor module located within the interior of the housing structure and an exterior portion of the first sensor module protruding through the exterior of the housing structure, the exterior portion of the first sensor module making contact with the wearer's wrist while the set of handcuffs is engaged in the locked position on the wearer, and the first sensor module comprising an $SpO_2$ sensor adapted to measure a first vitals measurement;
   (c) a second sensor module having an interior portion of the second sensor module located within the interior of the housing structure and an exterior portion of the second sensor module protruding through the exterior of the housing structure, the exterior portion of the second sensor module making contact with the wearer's wrist while the set of handcuffs is engaged in the locked position on the wearer, the second sensor module comprising a second sensor, other than the $SpO_2$ sensor, adapted to measure a second vitals measurement, and wherein this sensor is selected from the group consisting of a photoplethysmography sensor, a bioimpedance sensor, a dermal temperature sensor, an electrocardiogram sensor, and an electrodermal activity sensor;
   (d) a controller unit that is located within the interior of the housing structure, the controller unit being configured to relay instructional programs to the modules and units which cause the modules and units to operate, the controller unit receiving the first vitals measurement and the second vitals measurement from the first sensor module and second sensor module, respectively, and, upon detection of at least one of the first vitals measurement and the second vitals measurement outside of given parameters, producing at least one corresponding output signal related to the wearer's at least one of the first vitals measurement and the second vitals measurement outside of given parameters;
   (e) a communication unit that is located within the interior of the housing structure and receives the at least one corresponding output signal from the controller unit and is adapted to relay the at least one corresponding output signal to the law enforcement official to alert the law enforcement official of the wearer's medical issue via a speaker; and (f) a rechargeable power unit located within the interior of the housing structure that is accessed by a port on the exterior of the housing structure, provides power to the vitals monitoring handcuff apparatus's other modules and units, and having a receiver which connects with an exterior power source via the port.

2. The vitals monitoring apparatus coupled with a set of handcuffs of claim 1, wherein the second sensor module comprises a photoplethysmography sensor to measure the second vitals measurement which is the wearer's heart rate and relays that data to the controller unit.

3. The vitals monitoring apparatus coupled with a set of handcuffs of claim 2, further comprising a third sensor module having an interior portion of the third sensor module located within the interior of the housing structure and an exterior portion of the third sensor module protruding through the exterior of the housing structure, the exterior portion of the third sensor module making contact with the wearer's wrist while the set of handcuffs is engaged in the locked position on the wearer, and the third sensor module comprising a bioimpedance sensor adapted to measure a third vitals measurement and relay that data to the controller unit which, upon detection of the third vitals measurement outside of given parameters, produces at least one corresponding output signal for the third vitals measurement to send to the communication unit.

4. The vitals monitoring apparatus coupled with a set of handcuffs of claim 3, further comprising a fourth sensor module which is an ambient temperature sensor having an interior portion of the fourth sensor module located within the interior of the housing structure and an exterior portion of the fourth sensor module protruding through the exterior of the housing structure, and the fourth sensor module measuring and relaying the ambient temperature to the controller unit.

5. The vitals monitoring apparatus coupled with a set of handcuffs of claim 4, further comprising a GPS module that is located within the interior of the housing structure and is adapted to send location data to the controller unit.

6. The vitals monitoring apparatus coupled with a set of handcuffs of claim 5, further comprising a display unit on the exterior of the housing structure that displays the wearer's at least one vitals measurement received from the communication unit to visually alert the law enforcement official of the wearer's medical issue.

7. The vitals monitoring apparatus coupled with a set of handcuffs of claim 6, wherein the communication unit transmits the wearer's at least one vitals measurement and medical issue to an external receiver capable of alerting the law enforcement official of the wearer's medical issue and wherein the communication unit includes at least one unit selected from the group consisting a Bluetooth™ communicator, a mobile network communicator, a Wi-Fi™ communicator, and combinations thereof.

8. The vitals monitoring apparatus coupled with a set of handcuffs of claim 4, further comprising a display unit on the exterior of the housing structure that displays the wearer's at least one vitals measurement and visually alerts the law enforcement official of the wearer's medical issue.

9. The vitals monitoring apparatus coupled with a set of handcuffs of claim 8, wherein the communication unit transmits the wearer's at least one vitals measurement and medical issue to an external receiver that can alert the law enforcement official of the wearer's medical issue and wherein the communication unit includes at least one unit selected from the group consisting a Bluetooth™ communicator, a mobile network communicator, a Wi-Fi™ communicator, and combinations thereof.

10. The vitals monitoring apparatus coupled with a set of handcuffs of claim 4, wherein the housing structure is constructed to provide tamper and damage protection to the protruding exterior portions of the first sensor module, the second sensor module, the third sensor module, and the fourth sensor module.

11. The vitals monitoring apparatus coupled with a set of handcuffs of claim 1, wherein the housing structure is configured to allow one, unconnected cuff of the set of handcuffs to be coupled with the housing structure before attaching a connection portion to the coupled cuff through a connection hole in the housing structure to connect the coupled cuff to the other cuff of the set of handcuffs.

12. The vitals monitoring apparatus coupled with a set of handcuffs of claim 1, further comprising a functionality button on the housing structure.

13. A vitals monitoring handcuff apparatus comprising:
(a) a set of handcuffs used by a law enforcement official for detainment of a wearer and having an attached housing structure, the housing structure having an exterior and interior, the interior of the housing structure containing a plurality of modules and units, the exterior of the housing structure being constructed to generally have a complimentary shape to the set of handcuffs, and the exterior of the housing structure configured to contact the wearer's wrist during detainment while the set of handcuffs is engaged in a locked position on the wearer's wrist;
(b) a first sensor module having an interior portion of the first sensor module located within the interior of the housing structure and an exterior portion of the first sensor module protruding through the exterior of the housing structure, the exterior portion of the first sensor module making contact with the wearer's wrist while the set of handcuffs is engaged in the locked position on the wearer, and the first sensor module comprising an $SpO_2$ sensor adapted to measure a first vitals measurement;
(c) a second sensor module that is-having an interior portion of the second sensor module located within the interior of the housing structure and an exterior portion of the second sensor module protruding through the exterior of the housing structure, the exterior portion of the second sensor module making contact with the wearer's wrist while the set of handcuffs is engaged in the locked position on the wearer, the second sensor module comprising another sensor, other than an $SpO_2$ sensor, adapted to measure a second vitals measurement, and wherein this sensor is selected from the group consisting of a photoplethysmography sensor, a bioimpedance sensor, a dermal temperature sensor, an electrocardiogram sensor, and an electrodermal activity sensor;
(d) a controller unit that is located within the interior of the housing structure, the controller unit being configured to relay instructional programs to the modules and units which cause the modules and units to operate, the controller unit receiving the first vitals measurement and the second vitals measurement from the first sensor module and second sensor module, respectively, and, upon detection of at least one of the first vitals measurement and second vitals measurement outside of given parameters, producing at least one corresponding output signal related to the wearer's at least one of the first vitals measurement and the second vitals measurement outside of given parameters;

(e) a communication unit that is located within the interior of the housing structure and receives the at least one corresponding output signal from the controller unit and is adapted to relay the at least one corresponding output signal to the law enforcement official to alert the law enforcement official of the wearer's medical issue via a speaker; and (f) a rechargeable power unit located within the interior of the housing structure that is accessed by a port on the exterior of the housing structure, provides power to the vitals monitoring handcuff apparatus's other modules and units, and having a receiver which connects with an exterior power source via the port.

14. The vitals monitoring handcuff apparatus of claim 13, wherein the second sensor module comprises a photoplethysmography sensor to measure the second vitals measurement which is the wearer's heart rate and relays that data to the controller unit.

15. The vitals monitoring apparatus coupled with a set of handcuffs of claim 14, wherein the housing structure further comprises at least one access panel which, when the housing structure is uncoupled from the set of handcuffs, provides access to the modules and units that are within the housing structure.

16. The vitals monitoring handcuff apparatus of claim 13, further comprising a third sensor module having an interior portion of the third sensor module located within the interior of the housing structure with an exterior portion of the third sensor module protruding through the exterior of the housing structure, the exterior portion of the third sensor module making contact with the wearer's wrist while the set of handcuffs is engaged in the locked position on the wearer, and the third module comprising a bioimpedance sensor adapted to measure a third vitals measurement and relay that data to the controller unit which, upon detection of the third vitals measurement outside of given parameters, produces at least one corresponding output signal for the third vitals measurement to send to the communication unit.

17. The vitals monitoring handcuff apparatus of claim 16, further comprising a GPS module that is located within the interior of the housing structure and is adapted to send location data to the controller unit.

18. The vitals monitoring handcuff apparatus of claim 17, further comprising a display unit on the exterior of the housing structure that displays the wearer's at least one vitals measurement received from the communication unit and visually alerts the law enforcement official of the wearer's medical issue.

19. The vitals monitoring handcuff apparatus of claim 18, wherein the communication unit transmits the wearer's at least one vitals measurement and medical issue to an external receiver that can alert the law enforcement official of the wearer's medical issue and wherein the communication unit includes at least one unit selected from the group consisting of a Bluetooth™ communicator, a mobile network communicator, a Wi-Fi™ communicator, and combinations thereof.

20. The vitals monitoring handcuff apparatus of claim 16, wherein the housing structure is constructed to provide tamper and damage protection to the protruding exterior portions of the first sensor module, the second sensor module, and the third sensor module.

21. The vitals monitoring handcuff apparatus of claim 20, wherein the housing structure further comprises at least one access panel which provides access to the modules and units that are within the housing structure.

22. The vitals monitoring handcuff apparatus of claim 13, further comprising a functionality button on the housing structure.

* * * * *